United States Patent [19]

Nakagawa et al.

[11] Patent Number: 5,652,382

[45] Date of Patent: Jul. 29, 1997

[54] HUMIDITY METER

[75] Inventors: Shiro Nakagawa; Atsuko Tsuchida; Eiji Takahashi; Kenji Aizawa, all of Tokyo, Japan

[73] Assignee: TDK Corporation, Tokyo, Japan

[21] Appl. No.: 473,209

[22] Filed: Jun. 7, 1995

[30] Foreign Application Priority Data

Jun. 16, 1994 [JP] Japan ..................... 6-134705

[51] Int. Cl.6 .................... G05D 22/00; G01W 1/00
[52] U.S. Cl. .................. 73/335.02; 73/335.05; 73/29.02; 73/29.05; 324/678; 324/694
[58] Field of Search ............... 73/335.02, 335.05, 73/29.02, 29.05, 29.01; 324/694, 678

[56] References Cited

U.S. PATENT DOCUMENTS

| | | | |
|---|---|---|---|
| 4,546,916 | 10/1985 | Tsuaki | 236/44 A |
| 4,662,220 | 5/1987 | Laue | 73/336.5 |
| 4,816,748 | 3/1989 | Tazawa et al. | 324/694 |
| 4,915,816 | 4/1990 | Shakkottai et al. | 204/430 |
| 5,065,625 | 11/1991 | Nakagawa et al. | 73/336.5 |
| 5,317,274 | 5/1994 | Nakagawa et al. | 324/678 |

FOREIGN PATENT DOCUMENTS 1 507 568  4/1978  United Kingdom .

Primary Examiner—Hezron E. Williams
Assistant Examiner—J. David Wiggins
Attorney, Agent, or Firm—Oblon, Spivak, McClelland, Maier & Neustadt, P.C.

[57] ABSTRACT

An oscillator circuit includes a gate $G_{11}$ of C-MOS type ($Q_1$, $Q_2$, and the like) having the function of increasing an operating current i with increasing operating frequency. A humidity sensor HS changing electric impedance thereof in accordance with humidity is arranged in part of the oscillator circuit. The oscillator circuit converts a change in humidity into a change in frequency, causes the gate $G_{11}$ to convert the change in frequency into a change in operating current i, and outputs the converted change in operating current i. Further, in order to increase the change in operating current i due to the change in frequency, a series circuit consisting of a capacitor $C_{13}$ and a resistor $R_{17}$ is connected to the gate $G_{11}$ as a capacitive load.

6 Claims, 11 Drawing Sheets

$T_2 - T_3$ : OUTPUT $T_2 - T_3$ : OUTPUT

HUMIDITY METER

BACKGROUND OF THE INVENTION

The invention pertains to humidity meters used for detecting humidity in various types of electronic apparatuses, electric apparatuses, toys, home electric appliances, and the like. The invention is directed, in particular, to a humidity meter formed by integrating both an oscillator circuit including a humidity sensor and peripherals thereof.

FIGS. 14A, 14B and 15 are diagrams showing a conventional example. In these drawings, reference numeral 1 denotes a humidity-frequency converting circuit; 2, a differentiating circuit; 3, a waveform shaping circuit; 4, an integrating circuit; and 5, a threshold control circuit; and reference characters $R_1$ to $R_5$ denote resistors; $C_1$, $C_2$, capacitors; $G_1$, a gate; and Tr, a transistor.

FIG. 14A illustrates a block diagram of a conventional humidity meter; and FIG. 14B shows a waveform diagram of various parts of the humidity meter. Humidity meters have heretofore been used to detect humidity in various electronic apparatuses (e.g., copying machines, printers) and the like. One such humidity meter is shown.

As shown in FIG. 14A, this humidity meter includes: the humidity-frequency converting circuit 1; the differentiating circuit 2; the waveform shaping circuit 3; the integrating circuit 4; and the threshold control circuit 5. This humidity meter is designed to produce an output (a detected humidity) from the integrating circuit 4.

The humidity-frequency converting circuit 1 is formed by using an impedance variable humidity sensor that changes impedance exponentially in accordance with the change of humidity, and outputs a pulse train obtained by converting a change in humidity into a change in frequency.

The differentiating circuit 2 is a circuit for receiving the output pulse train from the humidity-frequency converting circuit 1 and differentiating the received pulse train to generate a pulse train whose width is narrower than that of the aforementioned pulse train. The waveform shaping circuit 3 is a circuit (threshold circuit) for extracting a differentiated wave component whose threshold level is not less than a predetermined threshold level out of the differentiated wave and shaping the waveform of the extracted wave component.

The integrating circuit 4 is designed to integrate the pulse train whose waveform has been shaped by the waveform shaping circuit 3. The threshold control circuit 5 controls the threshold level of the waveform shaping circuit 3 in response to the output voltage of the integrating circuit 4.

The operation of the humidity meter will be described below with reference to FIG. 14B. Outputted from the humidity-frequency converting circuit 1 are a pulse train whose frequency f is low on the low humidity side and a pulse train whose frequency f is high on the high humidity side (see S1). Then, these pulse trains are differentiated by the differentiating circuit 2. Each of these differentiated pulse trains (see S2) is subjected to an extracting process in which inch component whose threshold level is not less than a predetermined threshold level is extracted, and each extracted component is then subjected to a waveform shaping process by the waveform shaping circuit 3 (see S3). These waveform-shaped pulse trains are thereafter integrated by the integrating circuit 4 to obtain a humidity meter output.

Further, the output voltage of the integrating circuit 4 is applied to the threshold control circuit 5 as a control voltage, and it is with this control voltage that the threshold control circuit 5 controls the threshold level of the waveform shaping circuit 3.

The linearity of the humidity meter output is thus controlled by constantly optimizing a threshold level with respect to the magnitude of a humidity meter output in this way, and as a result, a humidity meter output with an excellent characteristic can be obtained.

FIG. 15 is an exemplary conventional humidity meter circuit. The circuit configuration of a specific example of the humidity meter is illustrated in FIG. 15.

This example is constructed by the differentiating circuit 2 of the capacitor $C_1$ and the resistor $R_1$; the waveform shaping circuit 3 of the gate (buffer gate) $G_1$; the threshold control circuit 5 of the transistor Tr and the resistors $R_2$, $R_3$; and the integrating circuit 4 of the capacitor $C_2$ and the resistor $R_5$.

The output voltage of the capacitor $C_2$ constituting the integrating circuit 4 is applied to the base of the transistor Tr constituting the threshold control circuit 5 through the resistor $R_4$.

As a result of this configuration, the base current of the transistor Tr is changed by the output voltage of the integrating circuit 4, and this changes the collector-emitter resistance of the transistor Tr in accordance with the output voltage of the integrating circuit 4. As a result, the potential on the input side of the gate $G_1$ is changed, thereby changing the threshold level.

In the aforementioned conventional humidity meter has addressed the following problems.

The aforementioned conventional humidity meter, which is of high accuracy type, requires the humidity-frequency converting circuit, the differentiating circuit, the waveform shaping circuit, the integrating circuit, the threshold control circuit, and the like. Therefore, the humidity meter formed by integrating these individual circuits is disadvantageous in that the number of parts is large and that needs for downsizing, lightening, and cost reduction are not easily met.

The aforementioned conventional humidity meter requires a large number of parts and uses expensive semiconductive elements particularly for the waveform shaping circuit and the threshold control circuit. Therefore, it is difficult to curtail the cost of manufacture, meaning that the humidity meter is expensive.

The downsizing of a humidity meter or the cost reduction of the humidity meter at the sacrifice of detection accuracy cannot be implemented by the aforementioned conventional humidity meter. That is, a humidity meter of extremely small structure or extremely low cost is difficult to implement out of the configuration of the conventional humidity meter. Therefore, it is difficult to meet the aforementioned needs.

SUMMARY OF THE INVENTION

The invention has been made to overcome these conventional problems, and the object of the invention is therefore to provide a humidity meter that is downsized, lighter in weight, and less expensive by reducing the number of parts.

A humidity meter according to the present invention comprises an oscillator circuit including an active circuit ($G_{11}$) having the function of increasing an operating current (i) in response to increasing operating frequency; the oscillator circuit having in part thereof a humidity sensor (HS) changing electric impedance thereof in response to humidity; the oscillator circuit converting a change in humidity into a change in frequency, further causing the active circuit to convert the change in frequency into a change in operating current (i), and outputting the converted operating current (i).

DETAILED DESCRIPTION OF PREFERRED EMBODIMENTS

Figure 1:
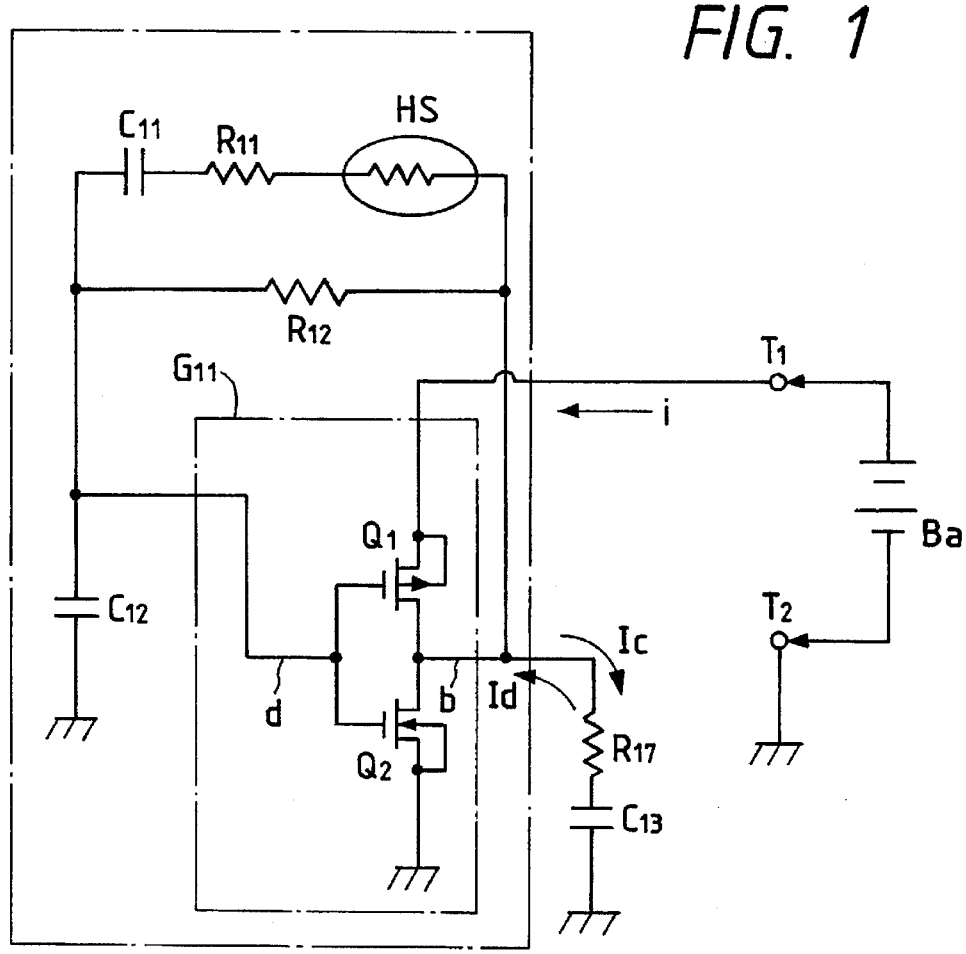
FIG. 1 is a diagram illustrative of the principle of the invention.

FIG. 1 is a diagram illustrative of the principle of the invention. In FIG. 1, reference characters $C_{11}$ to $C_{13}$ denote capacitors; $R_{11}$, $R_{12}$, $R_{17}$, resistors; HS, a humidity sensor; $T_1$, $T_2$, terminals; $Q_1$, a P-channel MOS-FET (MOS type field effect transistor); $Q_2$, an N-channel MOS-FET; $G_{11}$, a gate; and Ba, a power supply (battery).

To achieve the aforementioned object, a humidity meter of the invention has the following configuration. That is, in FIG. 1, the circuit consisting of the gate $G_{11}$, the resistor $R_{12}$, and the capacitor $C_{12}$ constitutes an astable multivibrator by a basic Schmitt trigger.

An oscillator circuit is formed by connecting a humidity sensor circuit that is constructed of a series circuit in parallel to the resistor $R_{12}$ constituting the aforementioned basic Schmitt trigger-based astable multivibrator, the series circuit consisting of the capacitor $C_{11}$, the resistor $R_{11}$, and the humidity sensor HS. The humidity meter is constructed of this oscillator circuit.

The humidity sensor HS is an impedance variable sensor. The impedance of the humidity sensor HS is high on the low humidity side, and drops rapidly on the high humidity side. The impedance of the humidity sensor HS changes nonlinearly with changing humidity.

Further, the gate $G_{11}$ is constructed of, e.g., a C-MOS integrated circuit (C-MOS logic circuit), and the output stage circuit thereof is such that two MOS-FETs $Q_1$, $Q_2$ are connected to each other in totem pole form. In this case, $Q_1$ is a P-channel MOS-FET, and $Q_2$ is an N-channel MOS-FET.

A series circuit consisting of the resistor $R_{17}$ and the capacitor $C_{13}$ (capacitive load) is connected to the output of the gate $G_{11}$ (active circuit) in order to increase change in operating current due to change in oscillating frequency. During the operation of the humidity meter, the power supply Ba is connected to the terminals $T_1$, $T_2$. At this instance, the voltage of the power supply Ba is applied to the output stage circuit consisting of $Q_1$, $Q_2$ to cause an operating current i to flow.

The operation of the invention based on the aforementioned configuration will be described with reference to FIG. 1.

The oscillator circuit oscillates at a frequency corresponding to a change in humidity. That is, when the humidity surrounding the humidity sensor HS changes, so does the impedance of the humidity sensor HS. This change in impedance leads to a change in the time constant of the oscillator circuit, which in turn changes the oscillating frequency.

In this case, the oscillating frequency is determined by the time constant of the capacitor $C_{12}$, the resistor $R_{12}$, and the humidity sensor circuit ($C_{11}+R_{11}+HS$). Further, since the humidity sensor HS exhibits high impedance on the low humidity side and drops the impedance drastically on the high humidity side, the oscillating frequency on the low humidity side is low and high on the high humidity side.

By the way, the output stage circuit of the gate $G_{11}$ is operated in such a manner that when the input (point d) is high level "1", $Q_1$ turns off and $Q_2$ turns on and the output (point b) therefore becomes low level "0". The operating current i flowing through $Q_1$, $Q_2$ at this instance is almost equal to zero.

Further, when the input (point d) is low level "0", $Q_1$ turns on and $Q_2$ is turned off and the output (point b) therefore becomes high level "1". The operating current i flowing through $Q_1$, $Q_2$ at this instance is almost equal to zero. As described above, the operating current i flowing through $Q_1$, $Q_2$ is almost equal to zero when the input is either high or low.

However, when the input (point d) changes from level "0" to level "1", or from level "1" to level "0" continuously, there is a timing at which both $Q_1$, $Q_2$ are put in a state close to the state of being turned on, and it is at this timing that a large operating current i flows through $Q_1$, $Q_2$.

Thus, it is only at the timing when the input is switched that the operating current i flows through the gate $G_{11}$. Since input switching occurs frequently per unit time with respect to high frequency inputs, the operating current i becomes quite large accordingly.

Therefore, the operating current i changes depending on the operating frequency in the gate $G_{11}$. The oscillating frequency changes in accordance with a change in humidity in the oscillator circuit. Since this change in frequency leads to a change in operating frequency of the gate $G_{11}$, the operating current i changes in accordance with a change in humidity.

Therefore, the detection of a current corresponding to a change in humidity can be made by detecting the operating current i. That is, since the operating current i flowing through $Q_1$, $Q_2$ of the gate $G_{11}$ changes in accordance with a change in impedance of the humidity sensor HS, humidity can be detected by detecting the operating current i.

On the other hand, when $Q_1$, $Q_2$ are turned on/off by the input voltage, the following currents flow.

(1) When $Q_1$ is turned on, the capacitor $C_{13}$ charging current Ic flows through $Q_1$ of the series circuit consisting of the resistor $R_{17}$ and the capacitor $C_{13}$ in accordance with the time constant of the circuit, thereby charging the capacitor $C_{13}$ to the power supply potential.

(2) Then, when $Q_1$ is turned off and $Q_2$ is turned on, the charges stored in the capacitor $C_{13}$ are discharged through the resistor $R_{7\ and\ Q2}$, thereby causing the discharge current Id to flow through the series circuit consisting of the resistor $R_{17}$ and the capacitor $C_{13}$ in accordance with the time constant of the circuit.

(3) Every time the input switches, the operations (1) and (2) are repeated, so that the operating current i is increased in proportion to the capacitor $C_{13}$ charging current. This operating current i depends on the oscillating frequency of the oscillator circuit.

Further, when the resistance of the resistor $R_{17}$ is equal to 0, the operating current i becomes proportional to the oscillating frequency. When the operating current i is increased at a low frequency (at a low humidity), the operating current i becomes too large at a high frequency (at a high humidity).

When the resistance of the resistor $R_{17}$ is set to a predetermined value to overcome this problem, the operating current is determined by the resistor $R_{17}$ with respect to frequencies not less than a frequency $f_0$ defined by the time constant of the resistor $R_{17}$ and the capacitor $C_{13}$, thereby making the operating current not dependent on frequency. Hence, the increase in current on the high humidity side can be suppressed, thereby improving the linearity of the output characteristic.

As is apparent from the above, the humidity meter can be formed only of the oscillator circuit including the humidity sensor HS. Therefore, the number of parts is curtailed, which in turn contributes to the downsizing, lightening, and cost reduction of the humidity meter.

Further, the change in operating current due to a change in the oscillating frequency of the oscillator circuit can be increased by adding the current change amplifying capacitor $C_{13}$ to the oscillator circuit constituting the humidity meter. As a result of this configuration, the humidity meter can enjoy improved humidity detection accuracy and improved output characteristic.

Still further, the rate of increase in operating current i on the high humidity side can be reduced by connecting the resistor $R_{17}$ in series with the current change amplifying capacitor $C_{13}$, thereby contributing to the improvement of the linearity of the output characteristic.

First Embodiment

Embodiments of the invention will now be described with reference to the drawings.

Figure 3:
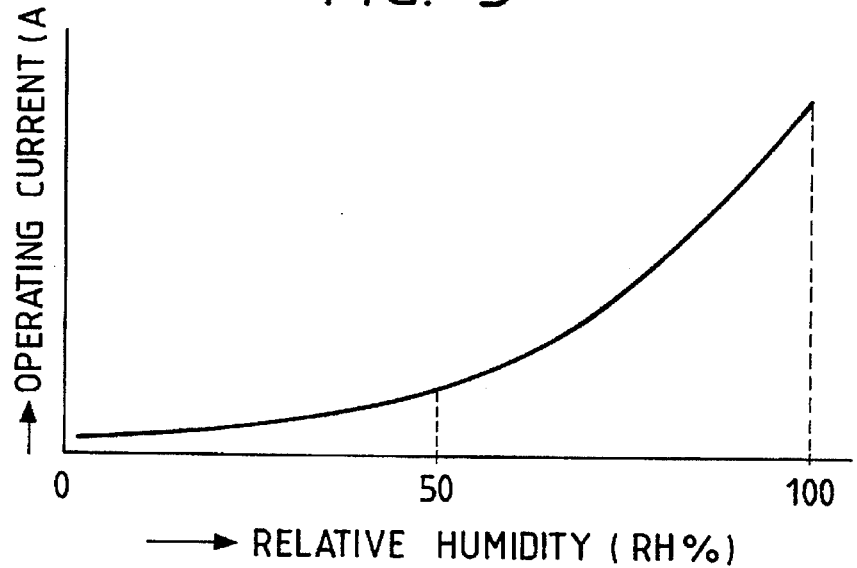
FIG. 3 is a diagram illustrative of the output characteristic of the first embodiment.
Figure 2A:
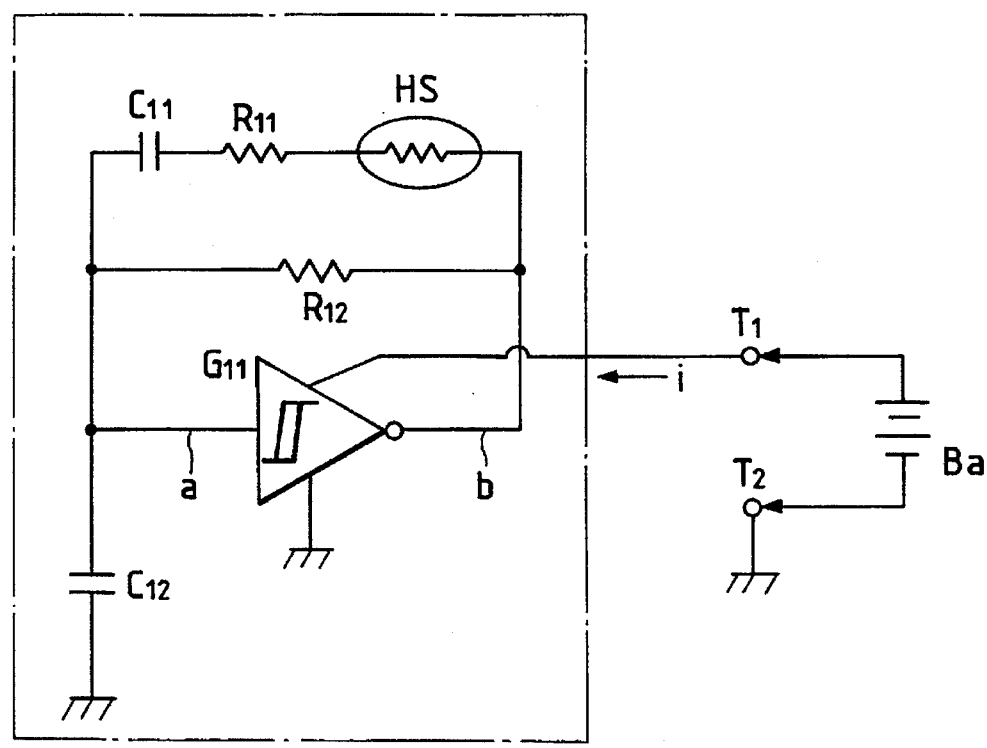
FIGS. 2A and 2B are diagrams illustrative of a first embodiment of the invention.
Figure 2B:
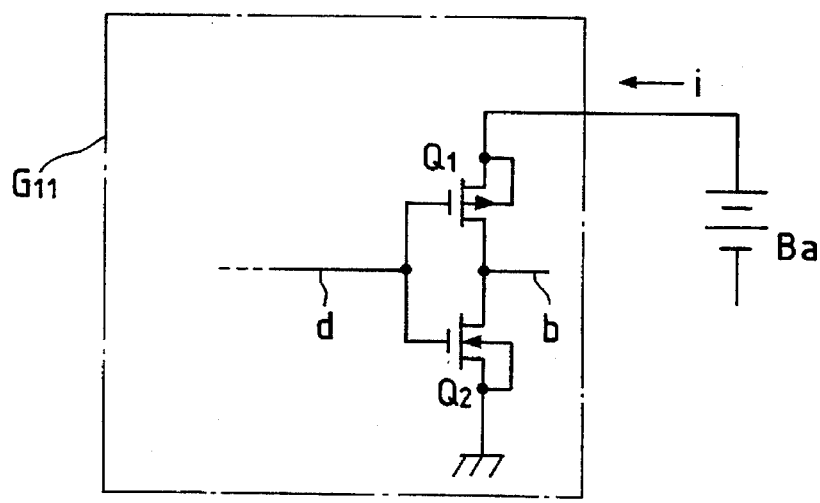

FIGS. 2A, 2B and 3 show the first embodiment. In these figures, reference characters $C_{11}$, $C_{12}$ denote capacitors; $R_{11}$, $R_{12}$, resistors; $G_{11}$, a gate (inverter gate); Ba, a power supply (battery); HS, a humidity sensor; and $T_1$, $T_2$, terminals (humidity meter terminals).

FIG. 2A is a circuit diagram of the humidity meter; and FIG. 2B is a diagram detailing part of FIG. 2A. The first embodiment is an example of a humidity meter utilizing an oscillator circuit that is constructed of a Schmitt trigger-based astable multivibrator (all the circuits are integrated).

In the circuits shown in FIGS. 2A and 2B, a circuit constructed of the gate $G_{11}$, the resistor $R_{12}$, and the capacitor $C_{12}$ is a basic Schmitt trigger-based astable multivibrator (basic oscillator circuit). In this circuit, the gate $G_{11}$ is a Schmitt trigger gate having a hysteresis characteristic; the capacitor $C_{12}$ is an oscillating capacitor; and the resistor $R_{12}$ is a bias resistor.

The oscillator, circuit is formed by connecting a humidity sensor circuit in parallel to the resistor $R_{12}$ of the basic Schmitt trigger-based astable multivibrator (basic oscillator circuit). The humidity sensor circuit is constructed of a series circuit consisting of the capacitor $C_{11}$, the resistor $R_{11}$, and the humidity sensor HS. It is the oscillator circuit itself that constitutes the humidity meter in the first embodiment.

In the humidity sensor circuit, the capacitor $C_{11}$ serves as a direct current interrupting capacitor (or direct current blocking capacitor), and the resistor $R_{11}$ serves as a resistor for correcting the characteristic of the humidity sensor HS on the high humidity side.

Further, the humidity sensor HS is an impedance variable sensor. The humidity sensor HS exhibits high impedance on the low humidity side, and the impedance drops drastically on the high humidity side (exponentially). The impedance of the humidity sensor HS changes nonlinearly with changing humidity.

The gate $G_{11}$ is constructed of a C-MOS integrated circuit. The output stage circuit thereof is, as shown in FIG. 2B, characterized as forming an inverter circuit in which two MOS-FETs $Q_1$, $Q_2$ are connected in totem pole form.

In this case, $Q_1$ is a P-channel MOS-FET, and $Q_2$ is an N-channel MOS-FET. To operate the humidity meter, the power supply (battery) Ba is connected to the terminals $T_1$, $T_2$ of the humidity meter. Upon connection of the battery Ba to the terminals $T_1$, $T_2$, the voltage of the power supply Ba is applied to the circuit consisting of $Q_1$, $Q_2$ to activate the humidity meter.

The oscillating operation of the oscillator circuit constituting the humidity meter is as follows. If it is assumed that the output (point b) of the gate $G_{11}$ (inverter) is high level "1", then the capacitor $C_{12}$ is charged through the resistor $R_{12}$.

This charging operation increases the terminal voltage of the capacitor $C_{12}$, and when this voltage (point a) reaches an upper threshold voltage of the Schmitt trigger in the gate $G_{11}$, the output (point b) of the gate $G_{11}$ goes low level "0".

Under this condition, the charges stored in the capacitor $C_{12}$ are discharged through the resistor $R_{12}$. Therefore, the input voltage of the gate $G_{11}$ starts to drop. When the input voltage reaches a lower threshold voltage, the output (point b) of the gate $G_{11}$ goes high level "1" again. Similar operations are repeated to oscillate the oscillator circuit.

Since the humidity sensor circuit ($C_1$+resistor $R_{11}$+HS) is connected in parallel to the resistor $R_{12}$, current flows through the humidity meter circuit when current flows through the resistor $R_{12}$. As a result, the oscillator circuit oscillates at a frequency corresponding to a change in humidity.

That is, when the humidity surrounding the humidity sensor HS changes, so does the impedance of the humidity sensor HS. This change in impedance leads to a change in the time constant of the oscillator circuit, which in turn changes the oscillating frequency.

In this case, the oscillating frequency is determined by the time constant of the capacitor $C_{12}$, the resistor $R_{12}$ and the humidity sensor circuit ($C_{11}$+$R_{11}$+HS). Further, the humidity sensor HS exhibits high impedance on the low humidity side, and drops the impedance thereof drastically on the high humidity side. Therefore, the oscillating frequency of the humidity sensor HS is low on the low humidity side and high on the high humidity side.

As shown in FIG. 2B, the output stage circuit of the C-MOS type IC is such that the two MOS-FETs $Q_1$, $Q_2$ are connected to each other in totem pole form. In this output stage circuit (inverter), when the input (point d) is high level "1", $Q_1$ turns off and $Q_2$ turns on and the output (point b) therefore becomes low level "0". The operating current i flowing through $Q_1$, $Q_2$ at this instance is almost equal to zero.

Further, when the input (point d) is low level "0", $Q_1$ turns on and $Q_2$ turns off and the output (point b) therefore becomes high level "1". The operating current i flowing through $Q_1$, $Q_2$ at this instance is almost equal to zero. As described above, the operating current i flowing through $Q_1$, $Q_2$ is almost equal to zero when the input is either high or low.

However, when the input (point d) changes from level "0" to level "1", or from level "1" to level "0" continuously, there is a timing at which both $Q_1$ and $Q_2$ are put in a state close to the state of being turned on, and it is at this timing that a large operating current i flows through $Q_1$, $Q_2$.

That is, it is only at the timing when the input switches that the operating current flows in the C-MOS type IC. Since input switching occurs frequently per unit time with respect to high frequency inputs, the operating current i becomes quite large accordingly.

Therefore, in the C-MOS type IC, the operating current i changes depending on the operating frequency. By the way, the oscillating frequency changes in accordance with a change in humidity in the oscillator circuit shown in FIG. 2A as described above. Such change in frequency leads to a change in the operating frequency of the gate $G_{11}$, which thus means that the operating current i changes in accordance with a change in humidity.

Hence, if the operating current i is detected, current corresponding to a change in humidity can be detected. That is, the operating current i flowing through $Q_1$, $Q_2$ of the gate $G_{11}$ changes in accordance with a change in the impedance of the humidity sensor HS, so that humidity can be detected by detecting the operating current i.

FIG. 3 is a diagram illustrative of the output characteristic of the first embodiment. The output characteristic (relative humidity-current characteristic) of the first embodiment will be described below with reference to FIG. 3. In FIG. 3, the horizontal axis indicates relative humidity (RH %), and the vertical axis indicates operating current (A).

As described above, the humidity meter according to the first embodiment is characterized as converting a change in humidity into a change in oscillating frequency, and further matching the change in frequency with a change in operating current i. The output characteristic of this case is, e.g., such as shown in FIG. 3.

As shown in FIG. 3, the operating current i is extremely small on the low humidity side, but the operating current i increases with increasing humidity and jumps drastically (exponentially) on the high humidity side. In this case, the relationship between humidity (relative humidity) and operating current i is nonlinear.

Since the operating current i changes with changing humidity as described above, humidity can be detected by detecting the operating current i. It may be noted that the operating current can be detected by, e.g., connecting a resistor to a return of the power supply circuit, causing the operating current i to be converted into voltage by this resistor, and outputting the converted voltage.

Second Embodiment

FIGS. 4A, 4B, 5A and 5B show the second embodiment. In these figures, the same parts and components as those in FIGS. 2 and 3 are denoted as the same reference characters. Further, in FIGS. 4A, 4B, 5A and 5B, reference characters $C_{13}$, $C_{14}$, $C_{15}$ denote capacitors; and $R_{13}$ and $R_{14}$, resistors.

Figure 4A:
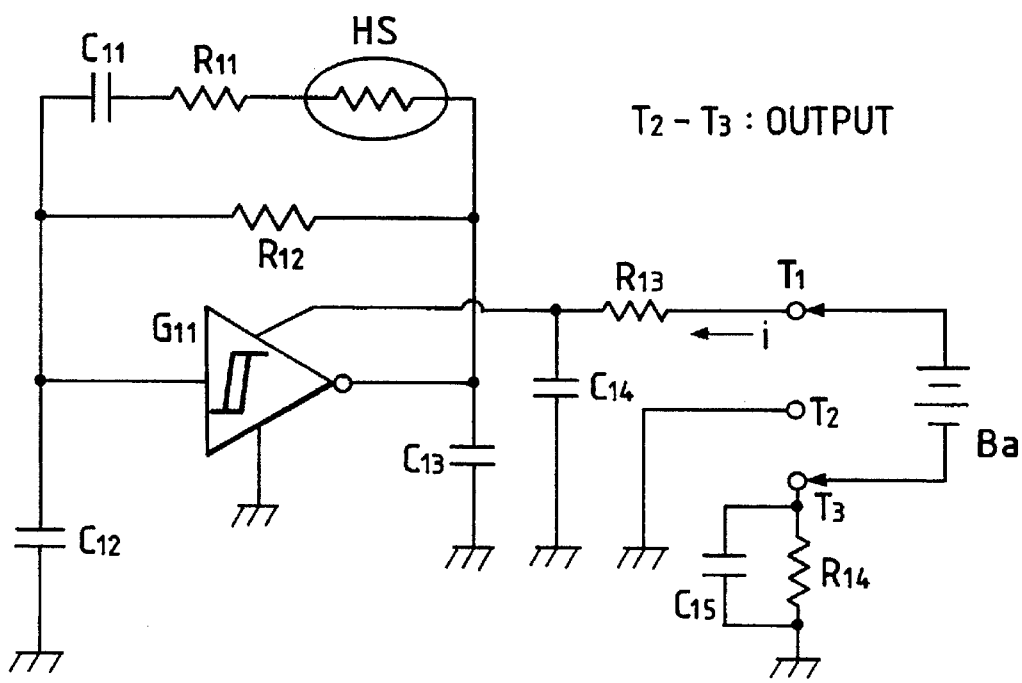
FIGS. 4A and 4B are diagrams illustrative of a second embodiment of the invention.
Figure 4B:
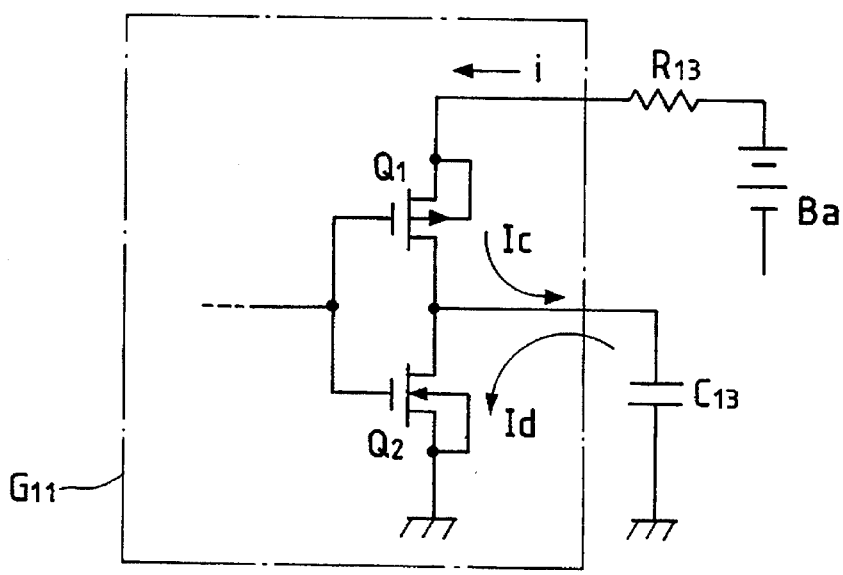

FIGS. 4A is a circuit diagram of the humidity meter, and FIG. 4B is a diagram detailing part of FIG. 4A. The second embodiment is an example in which a change in operating current due to a change in oscillating frequency is amplified and in which the linearity of the output characteristic of the humidity meter is improved in the humidity meter according to the first embodiment.

The humidity meter according to the second embodiment is formed by adding the capacitors $C_{13}$, $C_{14}$, $C_{15}$, and the resistors $R_{13}$, $R_{14}$, and the like to the humidity meter according to the first embodiment. The capacitor $C_{13}$ is an operating current change amplifying capacitor; the capacitors $C_{14}$, $C_{15}$ are bypass capacitors; the resistor $R_{13}$, an output limiting resistor; and the resistor $R_{14}$, a current-voltage converting resistor (a resistor for converting the operating current i into voltage).

In this humidity meter, terminals $T_1$, $T_2$, $T_3$ are arranged in such a manner that the power supply (battery) Ba is inserted between the terminals $T_1$, $T_3$ and that the terminal $T_2$ is grounded (connected to GND). Further, a parallel circuit consisting of the current-voltage converting resistor $R_{14}$ and the bypass capacitor $C_{15}$ is inserted between the terminal $T_3$ and GND (the return of the power supply circuit).

Still further, the output limiting resistor $R_{13}$ is connected to the terminal $T_1$, so that the voltage is supplied to the gate $G_{11}$ through this resistor $R_{13}$. The bypass capacitor $C_{14}$ is connected to the gate $G_{11}$.

As shown in FIG. 4B, MOS-FETs $Q_1$, $Q_2$ are connected to the output stage of the gate $G_{11}$ (in the same manner as in the first embodiment), and the operating current change amplifying capacitor $C_{13}$ is connected to the node of $Q_1$, $Q_2$ (the output of the gate $G_{11}$).

In the aforementioned configuration, the capacitor $C_{13}$ repeats charging and discharging so as to amplify the change in operating current i accompanied by the change in oscillating frequency (the operating current i is increased), whereas the resistor $R_{13}$ limits the operating current i that has been amplified too much so as to improve the linearity of the output characteristic.

Further, the terminals $T_2$, $T_3$ serve as output terminals. In this case, the resistor $R_{14}$ converts the operating current i into voltage, and the converted voltage is outputted as an output voltage of the humidity meter (a voltage corresponding to the humidity).

As described above, the capacitor $C_{13}$ is connected to the output of the gate $G_{11}$ so as to amplify the change in operating current i. The operating current amplifying effect of the capacitor $C_{13}$ will be described below.

(1) When $Q_1$ turns on, the capacitor $C_{13}$ is charged to the power supply potential by a current Ic flowing through $Q_1$.

(2) Then, when $Q_1$ turns off and $Q_2$ turns on, the charges stored in the capacitor $C_{13}$ are discharged through $Q_2$ so that a discharge current Id flows.

(3) Every time the input switches, the operations (1) and (2) are repeated, and the operating current i is therefore amplified in proportion to the capacitor $C_{13}$ charging current. This operating current i depends on the oscillating frequency of the oscillator circuit.

If it is assumed that the charges stored in the capacitor $C_{13}$ are Qc in the above operations, then the relationship, Qc=CV, is established (where C is the capacitance of the capacitor $C_{13}$, and V is the voltage of the capacitor $C_{13}$).

Since Qc is charged and discharged "f" times every second, the relationship, $i = f \cdot Qc$, is established.

Figure 5A:
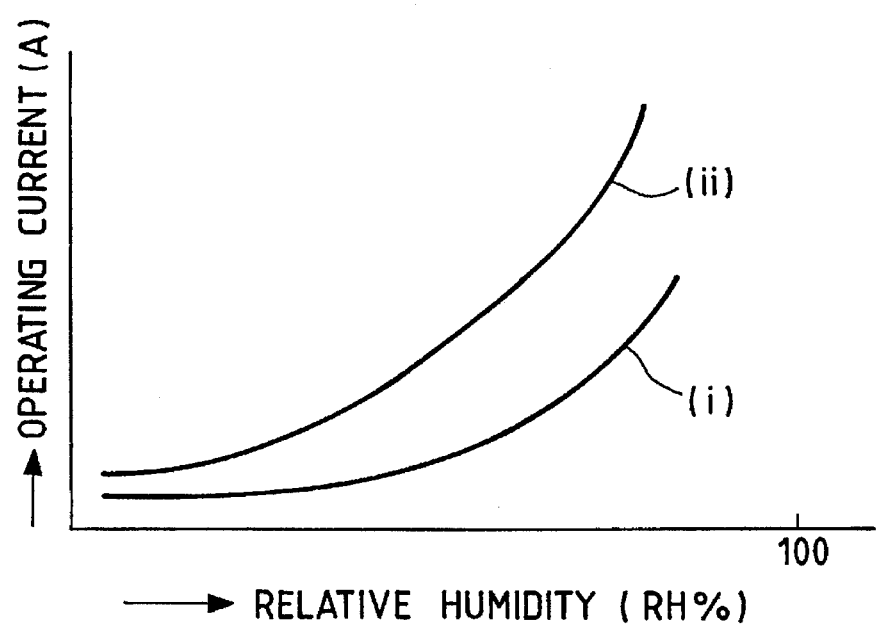
FIGS. 5A and 5B are diagrams illustrative of the output characteristic of the second embodiment.
Figure 5B:
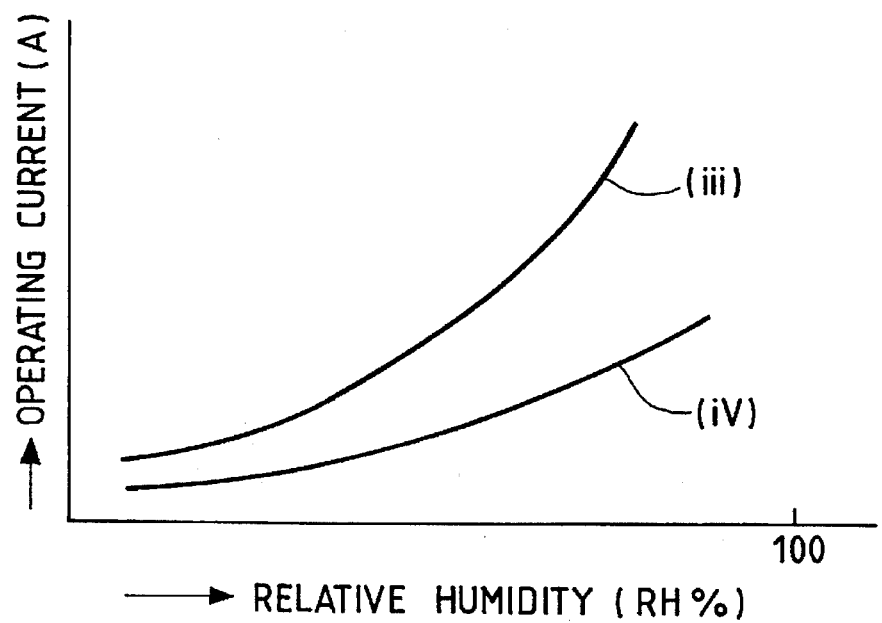

FIG. 5A shows a first exemplary output characteristic, and FIG. 5B shows a second exemplary output characteristic. The output characteristic (relative humidity-operating current characteristic) of the second embodiment will be described below with reference to FIGS. 5A and 5B.

(1) Description of the output characteristic brought about by the capacitor $C_{13}$ (see FIG. 5A)

In FIG. 5A, the horizontal axis indicates relative humidity (RH %), and the vertical axis indicates operating current (A). Further, a curve (i) depicts the output characteristic of the humidity meter without the resistor $R_{13}$ and the capacitor $C_{13}$ (the same characteristic as that of the first embodiment); and a curve (ii) depicts the output characteristic of the humidity meter with only the capacitor $C_{13}$ connected thereto.

When the resistor R13 and the capacitor C13 are not connected (the same condition as in the first embodiment), the operating current i is small and the linearity of the output characteristic is not satisfactory as indicated by the curve (i). However, when the capacitor $C_{13}$ is connected to the output of the gate $G_{11}$, the capacitor $C_{13}$ is charged and discharged, and as a result, a change in operating current i due to a change in the oscillating frequency of the oscillator circuit is amplified (the operating current i is increased) as indicated by the curve (ii).

(2) Description of the output characteristic brought about by the capacitor $C_{13}$ and the resistor $R_{13}$ In FIG. 5B, the horizontal axis indicates relative humidity (RH %), and the vertical axis indicates operating current (A). Further, a curve (iii) depicts the output characteristic of the humidity meter with only the capacitor $C_{13}$ connected thereto (the same characteristic as that of the curve (ii) in FIG. 5A), and a curve (iv) depicts the output characteristic of the humidity meter with both the resistor $R_{13}$ and the capacitor $C_{13}$ connected thereto (the same connecting condition as that shown in FIG. 4A).

As described above, when the capacitor $C_{13}$ is connected, the curve (iii) is obtained with a change in operating current i resulting from a change in the operating frequency of the oscillator circuit is amplified. When the resistor $R_{13}$ is additionally connected, the operating current i is limited by the resistor $R_{13}$, thereby producing the output characteristic with improved linearity as shown by the curve (iv).

Third Embodiment

Figure 6:
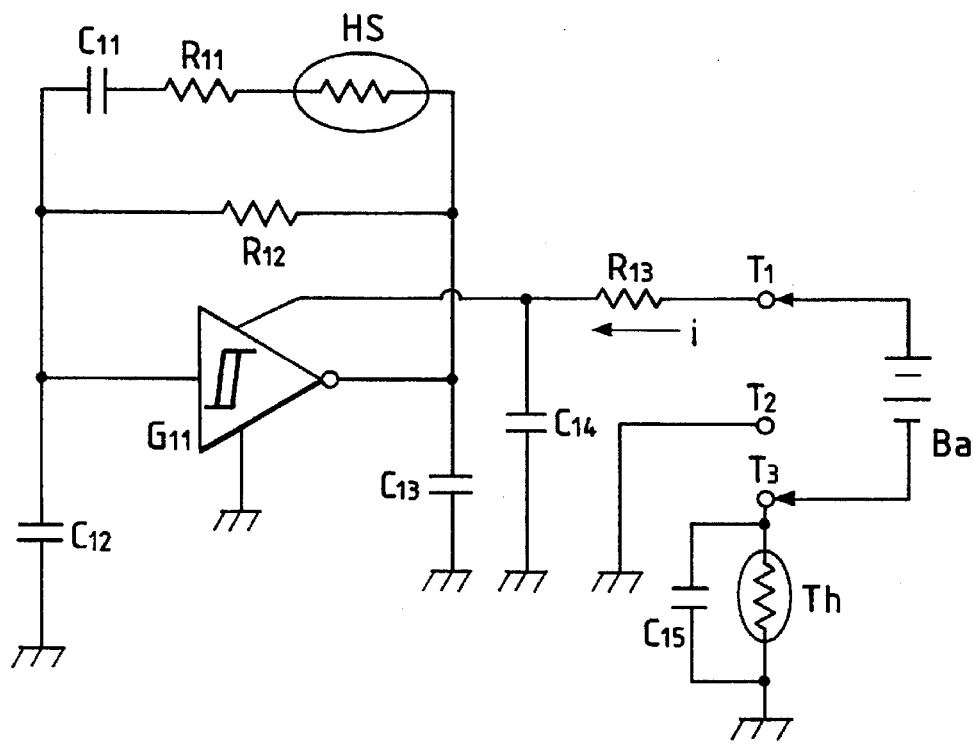
FIG. 6 is a diagram illustrative of a third embodiment of the invention.

FIG. 6 is a diagram illustrative of the third embodiment. In FIG. 6, the same parts and components as those in FIGS. 2 to 5 are denoted as the same reference characters. Reference character Th denotes a thermistor.

The third embodiment is an example in which the thermistor Th serves the double purpose of converting the operating current into voltage and making temperature compensation by replacing the resistor $R_{14}$ in the second embodiment with the thermistor Th.

By the way, the humidity meter according to the second embodiment is characterized as increasing the oscillating frequency with increasing temperature. That is, the operating current i increases with increasing temperature.

However, the thermistor Th exhibits high resistance at low temperatures, and reduces resistance with increasing temperature (negative temperature coefficient type). Therefore, although the operating current i increases with increasing temperature, the resistance of the thermistor Th decreases correspondingly, which in turn leaves the output voltage between the terminals $T_2$, $T_3$ (the voltage of the thermistor Th) little changed with increasing temperature.

If the thermistor Th is connected to the return of the power supply circuit in this way, not only the operating current i can be converted into voltage (the output voltage of the humidity meter) but also an increase in operating current i due to an increase in ambient temperature can be compensated for by the thermistor Th. Since other configurational aspects of the third embodiment are the same as those of the second embodiment except for the thermistor Th, the description of such other aspects will be omitted.

Fourth Embodiment

Figure 7:
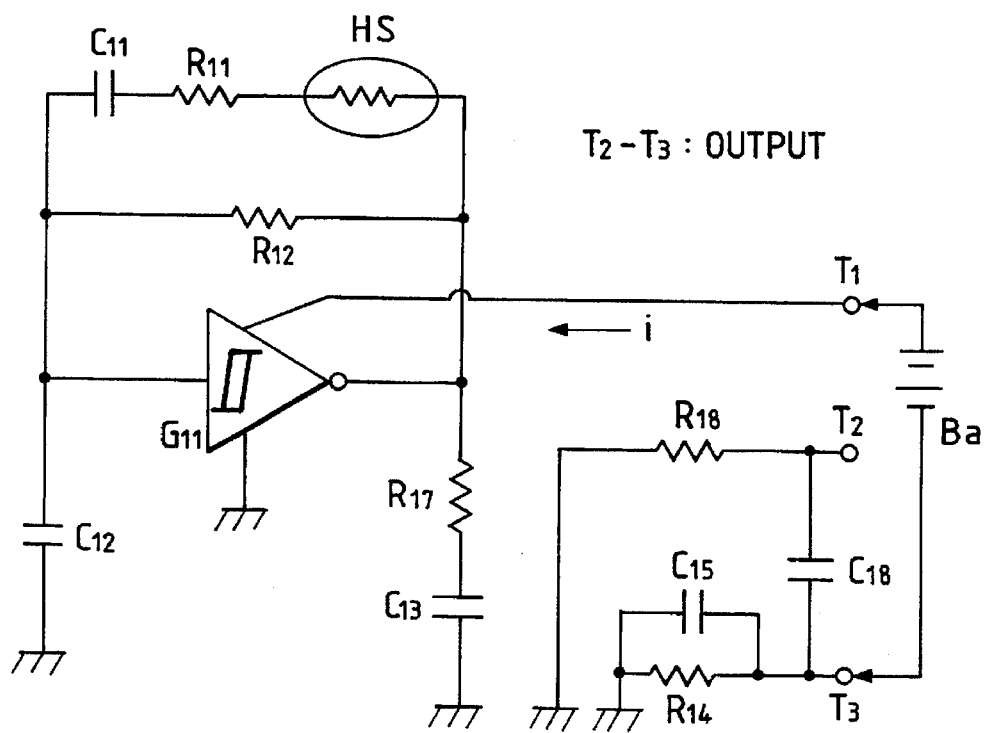
FIG. 7 is a diagram illustrative of a fourth embodiment of the invention.
Figure 8A:
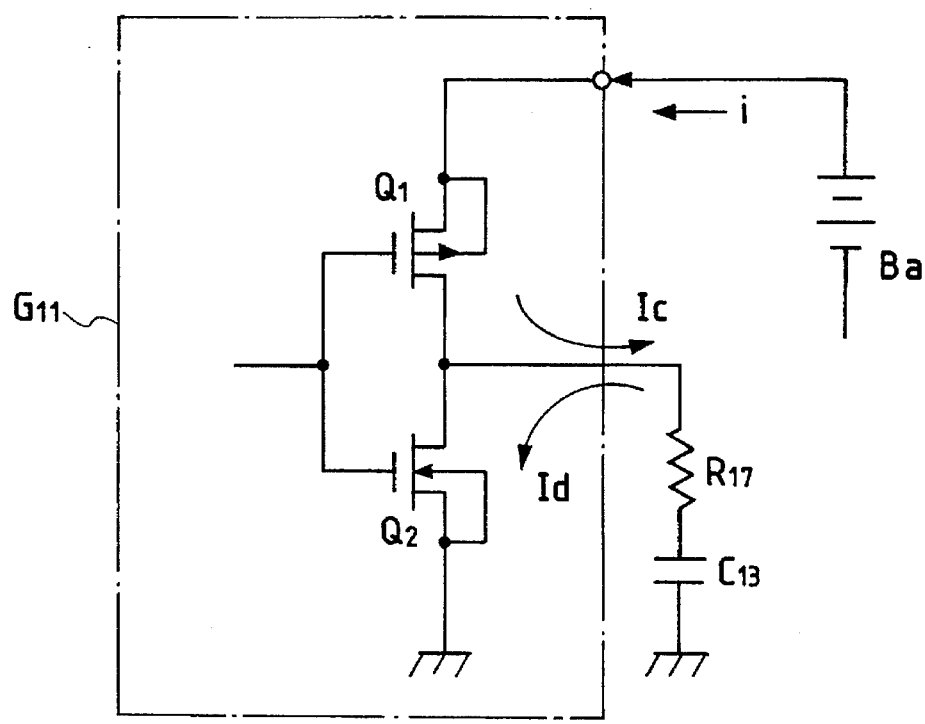
FIGS. 8A and 8B are diagrams illustrative of the operation of the fourth embodiment.
Figure 8B:
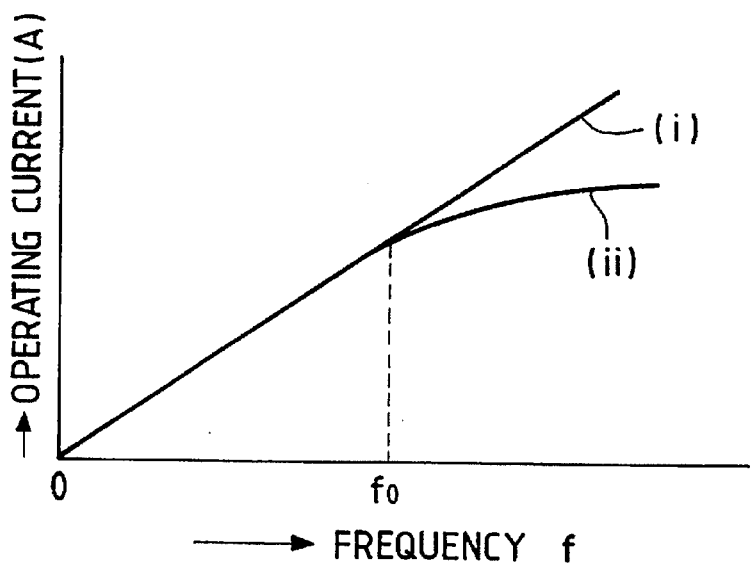
Figure 9:
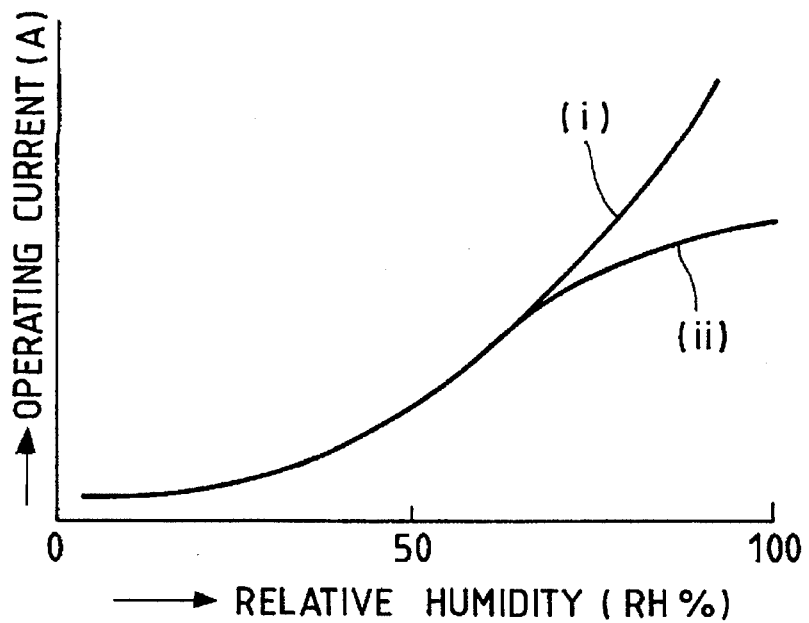
FIG. 9 is a diagram illustrative of the output characteristic of the fourth embodiment.

FIGS. 7 to 9 show the fourth embodiment. In FIGS. 7 to 9, the same parts and components as those in FIGS. 2 to 6 are denoted as the same reference characters. Reference characters $R_{17}$, $R_{18}$ denote resistors, and $C_{18}$, a capacitor.

FIG. 7 is a diagram illustrative of the fourth embodiment. The circuit configuration of a humidity sensor, which is the fourth embodiment of the invention, will be described with reference to FIG. 7.

The fourth embodiment is an example in which the linearity of the output characteristic of the humidity meter according to the second embodiment (see FIG. 5) is further improved. As shown in FIG. 7, the fourth embodiment is characterized not only as connecting the resistor $R_{17}$ in series with the capacitor $C_{13}$ but also as adding an output smoothing filter consisting of the resistor $R_{18}$ and the capacitor $C_{18}$ to the humidity meter according to the second embodiment.

When the capacitor $C_{13}$ is connected to the output side of the gate $G_{11}$ in the aforementioned configuration, the operating current i increases as described with reference to the second embodiment. In this case, the increase in operating current i brought about by the capacitor $C_{13}$ is proportional to the operating frequency of the gate $G_{11}$.

However, the rate at which the operating current i increases decreases at frequencies not less than a frequency ($f = 1/2\pi CR$) determined by the time constant CR (where C is the capacitance of the capacitor $C_{13}$, and R is the resistance of the resistor $R_{17}$) of the capacitor $C_{13}$ and the resistor $R_{17}$, according to the series circuit (capacitive load) consisting of the capacitor $C_{13}$ and the resistor $R_{17}$.

Therefore, by connecting the series circuit (capacitive load) consisting of the capacitor $C_{13}$ and the resistor $R_{17}$ to the output side of the gate $G_{11}$, the increase in operating current i on the high humidity side can be suppressed, which in turn improves the linearity of the output characteristic (the detail will be described later).

Further, since the output smoothing filter consisting of the resistor $R_{18}$ and the capacitor $C_{18}$ is added, the output voltage across the terminals $T_2$, $T_3$ is smoothed.

FIG. 8A is a partially detailed diagram of FIG. 7, and FIG. 8B is a diagram illustrative of the output characteristic (frequency-operating current characteristic). The operation performed by the resistor $R_{17}$ and the capacitor $C_{13}$ will be described below with reference to FIGS. 8A and 8B.

In FIG. 8A, when MOS-FETs $Q_1$, $Q_2$ are turned on and off by the input voltage, the current flows as follows (basically in the same manner as in the second embodiment except for the time constant at the charging and discharging time).

(1) When $Q_1$ turns on, the charging current Ic of the capacitor $C_{13}$ flows through $Q_1$ in accordance with the time constant (the time constant determined by the resistance of $R_{17}$ multiplied by the capacitance of $C_{13}$) of the series circuit consisting of the resistor R17 and the capacitor C13, so that the capacitor $C_{13}$ is charged to the power supply potential.

(2) Then, when $Q_1$ turns off and $Q_2$ turns on, the charges stored in the capacitor $C_{13}$ are discharged through the resistor $R_{17}$ and $Q_2$, thereby causing the discharge current Id to flow in accordance with the time constant of the circuit.

(3) Every time the input switches, the operations (1) and (2) are repeated, so that the operating current i is increased in proportion to the capacitor $C_{13}$ charging current. This operating current i depends on the oscillating frequency of the oscillator circuit.

By the way, if the resistance of the resistor $R_{17}$ is equal to zero, the operating current i is proportional to the oscillating frequency. If the operating current i is increased at a low frequency (at a low humidity), the operating current i becomes too large at a high frequency (at a high humidity).

To overcome this problem, if the resistance of the resistor $R_{17}$ is set to a certain value, the operating current i is regulated by the resistor $R_{17}$ with respect to frequencies not less than a frequency $f_0$ determined by the time constant of the circuit consisting of the resistor $R_{17}$ and the capacitor $C_{13}$, which means that the operating current i is no longer dependent on frequency. As a result, the increase in current on the high humidity side can be controlled. This condition is shown in FIG. 8B.

It may be noted that the frequency $f_0$ is such that $f_0 = 1/2\pi CR$, where C is the capacitance of the capacitor $C_{13}$, and R is the resistance of the resistor $R_{17}$. In FIG. 8B, a curve (i) depicts the output characteristic of the humidity meter with only the capacitor $C_{13}$ added thereto; and a curve (ii) depicts the output characteristic of the humidity meter with the resistor $R_{17}$ and the capacitor $C_{13}$ added thereto.

As is apparent from FIG. 8B, the output characteristic depicted by the curve (ii) is characterized as exhibiting a controlled operating current i at high frequencies (high humidity side) compared with the output characteristic depicted by the curve (i). This contributes to improving the linearity of the output characteristic.

FIG. 9 is a diagram illustrative of the output characteristic of the fourth embodiment. The output characteristic (relative humidity-operating current characteristic) of the fourth embodiment will be described below with reference to FIG. 9. In FIG. 9, the horizontal axis indicates relative humidity (RH %), and the vertical axis indicates the operating current (A). Further, a curve (i) depicts the output characteristic of the humidity meter with only the capacitor $C_{13}$ added thereto, and a curve (ii) depicts the output characteristic of the humidity meter with a series circuit consisting of the resistor $R_{17}$ and the capacitor $C_{13}$ added thereto.

As described above, the operating current i is increased when only the capacitor $C_{13}$ is added as depicted by the curve (i), but the linearity of the output characteristic is impaired (the operating current is excessively increased on the high humidity side). However, when the series circuit consisting of the resistor $R_f$ and the capacitor $C_{13}$ is added, the increase in operating current on the high humidity side can be suppressed as depicted by the curve (ii), and the linearity of the output characteristic can therefore be improved.

Fifth Embodiment

Figure 10:
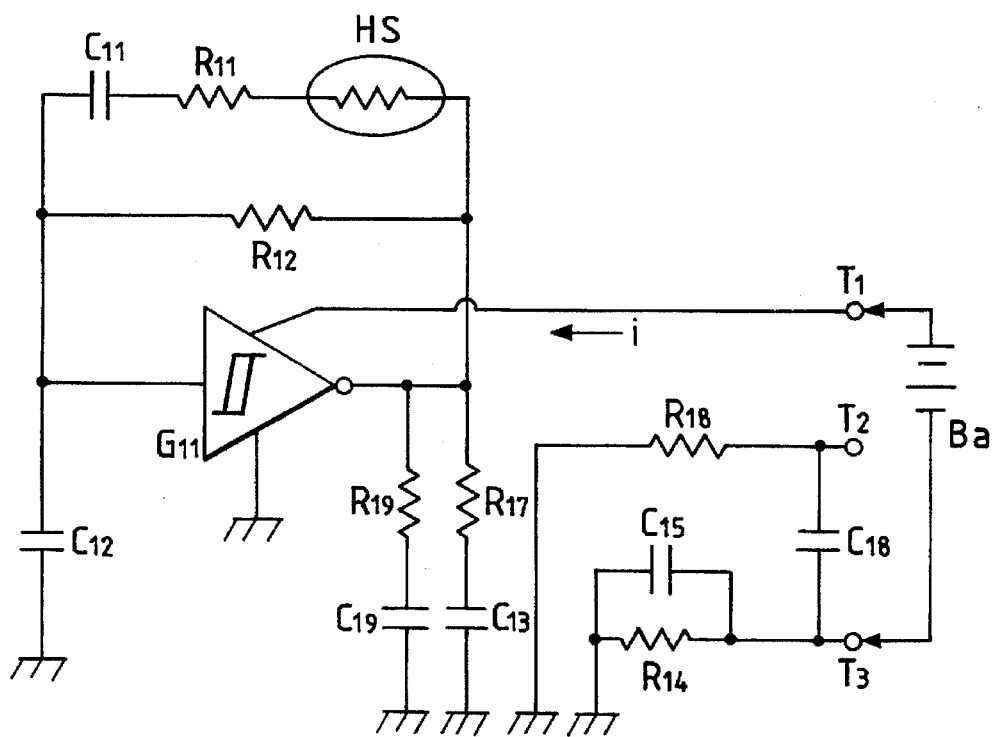
FIG. 10 is a diagram illustrative of a fifth embodiment of the invention.
Figure 11:
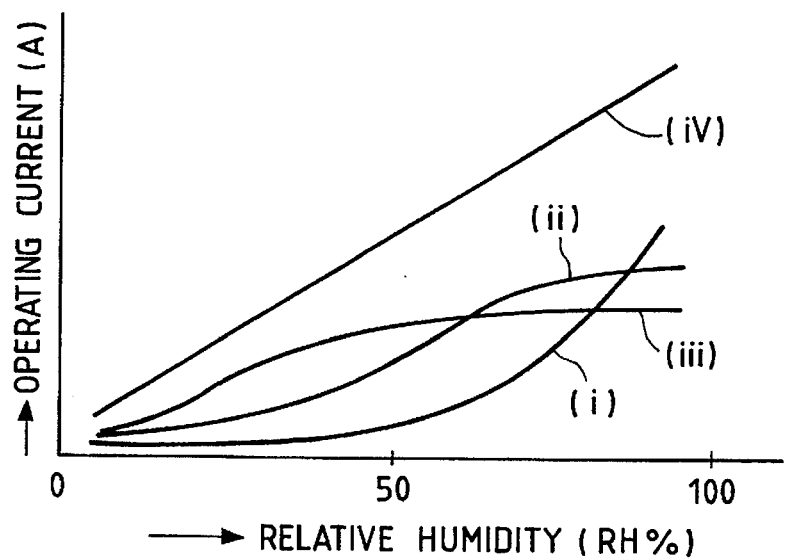
FIG. 11 is a diagram illustrative of the output characteristic of the fifth embodiment.
Figure 15:
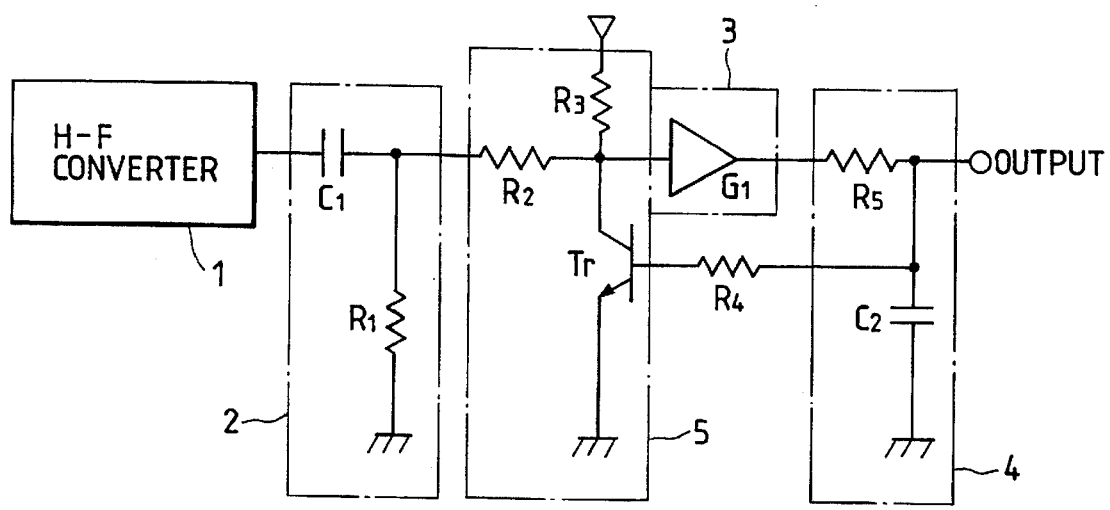
FIG. 15 is a diagram showing an exemplary conventional humidity meter circuit.

FIGS. 10 and 11 show the fifth embodiment. In FIGS. 10 and 11, the same parts and components as those in FIGS. 2 to 9 are denoted as the same reference characters. Further, reference character $R_{19}$ denotes a resistor; and $C_{19}$, a capacitor.

FIG. 10 is a diagram illustrative of the fifth embodiment. The circuit configuration of a humidity meter according to the fifth embodiment will be described below with reference to FIG. 10.

The fifth embodiment is an example in which in the fourth embodiment the series circuit consisting of the resistor $R_{17}$ and the capacitor $C_{13}$ is connected in parallel to a series circuit consisting of the resistor $R_{19}$ and the capacitor $C_{19}$ to further improve the linearity of the humidity meter.

As shown in FIG. 10, the series circuit consisting of the resistor $R_{17}$ and the capacitor $C_{13}$ (capacitive load) and the series circuit consisting of the resistor $R_{19}$ and the capacitor $C_{19}$ (capacitive load) are connected in parallel to each other to the output of the gate $G_{11}$. Thus, the linearity of the output characteristic of the humidity meter is improved by these two series circuits. It may be noted that other configurational aspects are the same as those in the fourth embodiment, and the description of such other aspects will therefore be omitted.

FIG. 11 is a diagram illustrative of the output characteristic of the fifth embodiment. The output characteristic (relative humidity-operating current characteristic) of the fifth embodiment will be described below with reference to FIG. 11.

In FIG. 11, the horizontal axis indicates relative humidity (RH %), and the vertical axis indicates operating current (A). Further, a curve (i) depicts the output characteristic of the humidity meter with the resistors ($R_{17}$, $R_{19}$) and the capacitors ($C_{13}$, $C_{19}$) not connected to the output of the gate $G_{11}$ (the same as in the first embodiment); a curve (ii) depicts the output characteristic with only the series circuit consisting of the resistor $R_{17}$ and the capacitor C13 connected to the output of the gate $G_{11}$ (the same as in the fourth embodiment); a curve (iii) depicts the output characteristic with only the series circuit consisting of the resistor $R_{19}$ and the capacitor C19 connected to the output of the gate $G_{11}$; and a curve (iv) depicts the output characteristic with the series circuit consisting of the resistor $R_{17}$ and the capacitor C13 and the series circuit consisting of the resistor $R_{19}$ and the capacitor C19 connected ((ii)+(iii)).

As shown in FIG. 11, the operating currents i are suppressed in high frequencies (on the high humidity side) in the output characteristics (ii), (iii) compared with that in the output characteristic (i) as described in the fourth embodiment. In the output characteristic (iv) in which the output characteristics (ii) and (iii) are combined, the linearity of the output characteristic can be further improved.

Sixth Embodiment

Figure 12A:
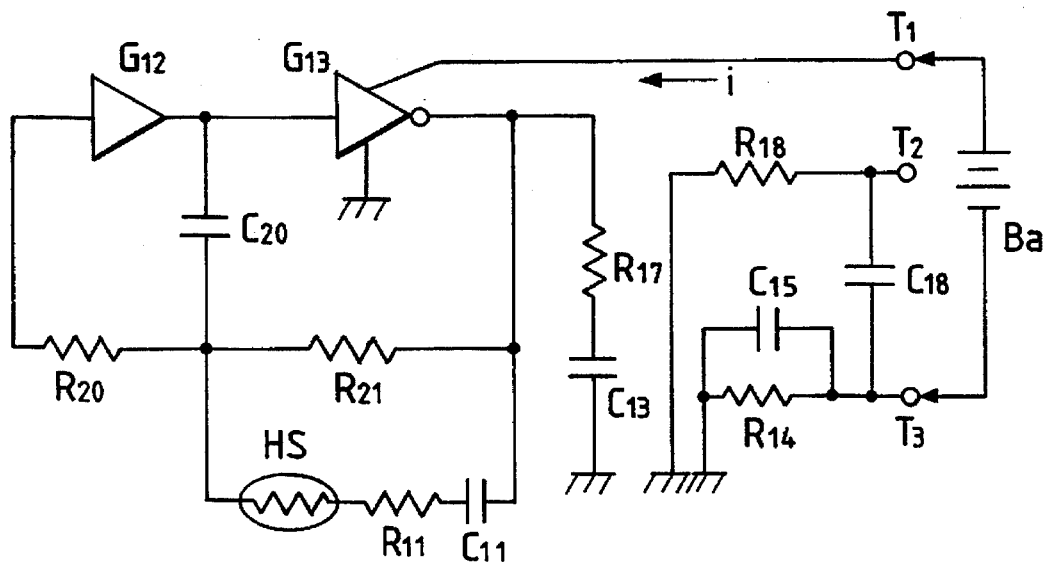
FIGS. 12A and 12B are diagrams illustrative of a sixth embodiment of the invention.
Figure 12B:
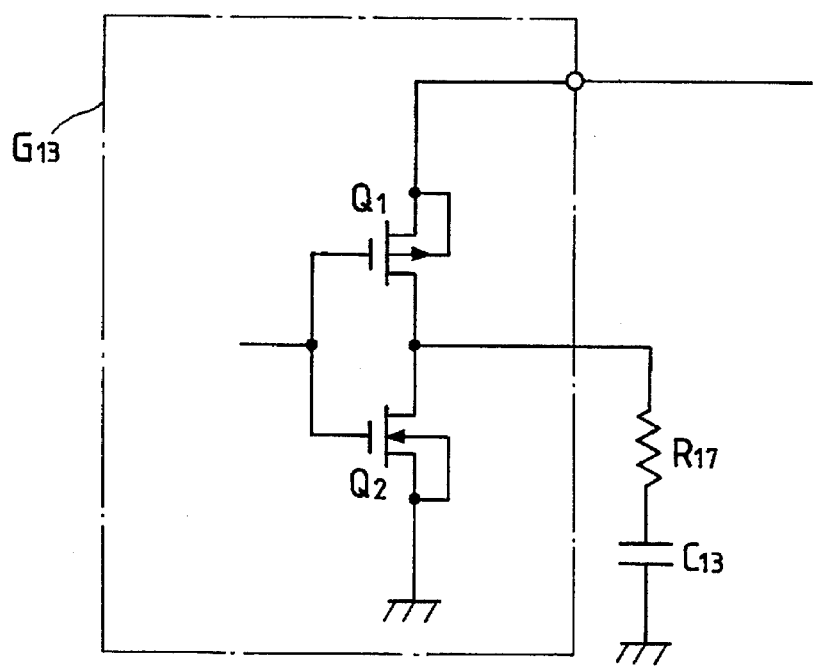

FIG. 12A is a circuit diagram of a humidity meter, and FIG. 12B is a diagram detailing part of FIG. 12A. In FIGS. 12A and 12B, the same parts and components as those in FIGS. 2 to 11 are denoted as the same reference characters. Further, reference characters $G_{12}$, $G_{13}$ denote gates; $R_{20}$, a resistor; and $C_{20}$, a capacitor.

The circuit configuration of the humidity meter according to the sixth embodiment will be described below with reference to FIGS. 12A and 12B. The sixth embodiment is an example in which the configuration of the oscillator circuit in the fourth embodiment is modified.

The oscillator circuit of the sixth embodiment is formed by connecting a humidity sensor circuit in parallel to the resistor $R_{12}$ of a basic oscillator circuit (a C-MOS gate-based astable multivibrator). The basic oscillator circuit consists of C-MOS gate ICs, the resistors $R_{20}$, $R_{12}$, and the capacitor $C_{20}$, the C-MOS gate ICs being constructed of the gate $G_{12}$ (buffer gate) and the gate $G_{13}$. The humidity sensor circuit consists of the humidity sensor HS, the resistor $R_{11}$, and the capacitor $C_{11}$.

In the aforementioned oscillator circuit, the resistor $R_{20}$ is a gate protecting resistor; and the resistor $R_{12}$ and the capacitor $C_{20}$ are elements for determining the oscillating frequency of the basic oscillator circuit. Further, the capacitor $C_{11}$ is a direct current interrupting (or direct current blocking) capacitor; and the resistor $R_{11}$ is a resistor for characteristic compensation of the humidity sensor HS on the high humidity side.

The aforementioned oscillator circuit oscillates at a frequency corresponding to a change in humidity in a manner similar to the respective embodiments. However, the oscillating frequency of this oscillator circuit is determined by the time constant based on the impedance of the capacitor $C_{20}$, the resistor $R_{12}$, and the humidity sensor circuit (HS+$R_{11}$+$C_{11}$).

It may be noted that the configurational aspects other than the oscillator circuit, being the same as those of the fourth embodiment, will not be described. While the gate $G_{11}$ in the fourth embodiment is denoted as the gate $G_{13}$ in the sixth embodiment, the gate $G_{13}$ is substantially the same as the gate $G_{11}$. In the sixth embodiment, also, a P-channel MOS-FET $Q_1$ and an N-channel MOS-FET $Q_2$ are connected in totem pole form to the output stage circuit of the gate $G_{13}$.

If it is assumed that the humidity surrounding the humidity sensor HS changes, then the impedance of the humidity sensor HS changes. This change in impedance changes the time constant, thereby changing the oscillating frequency. That is, the oscillator circuit oscillates at an oscillating frequency corresponding to the change in humidity.

As a result, an operating current corresponding to the change in humidity flows through the gate $G_3$ in a manner similar to the fourth embodiment, and the output voltage (the output of the humidity meter) corresponding to the change in humidity can be obtained across the terminals $T_2$, $T_3$.

Figure 13A:
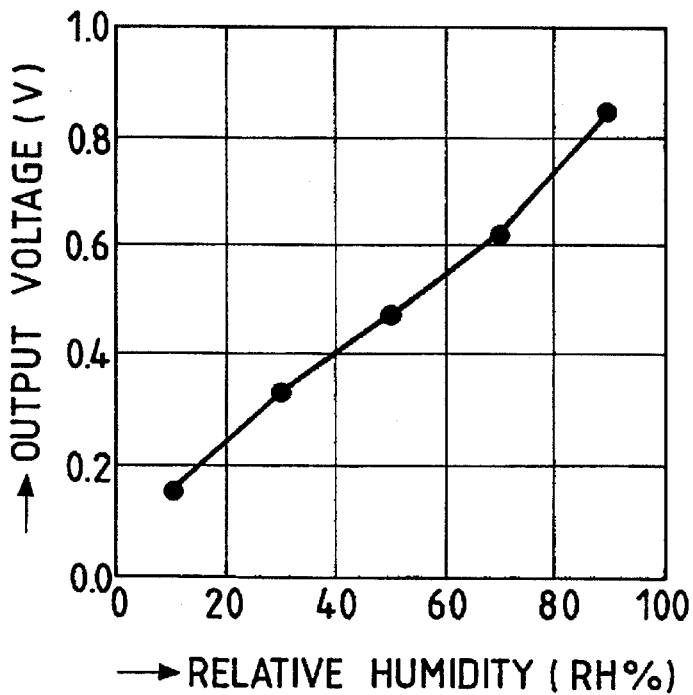
FIGS. 13A and 13B are diagrams showing exemplary measured data of the embodiments.
Figure 13B:
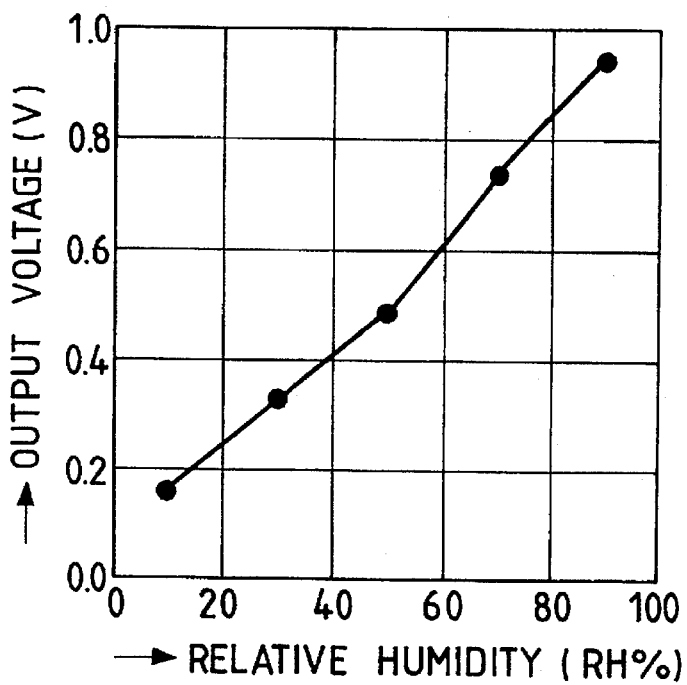
Figure 14A:
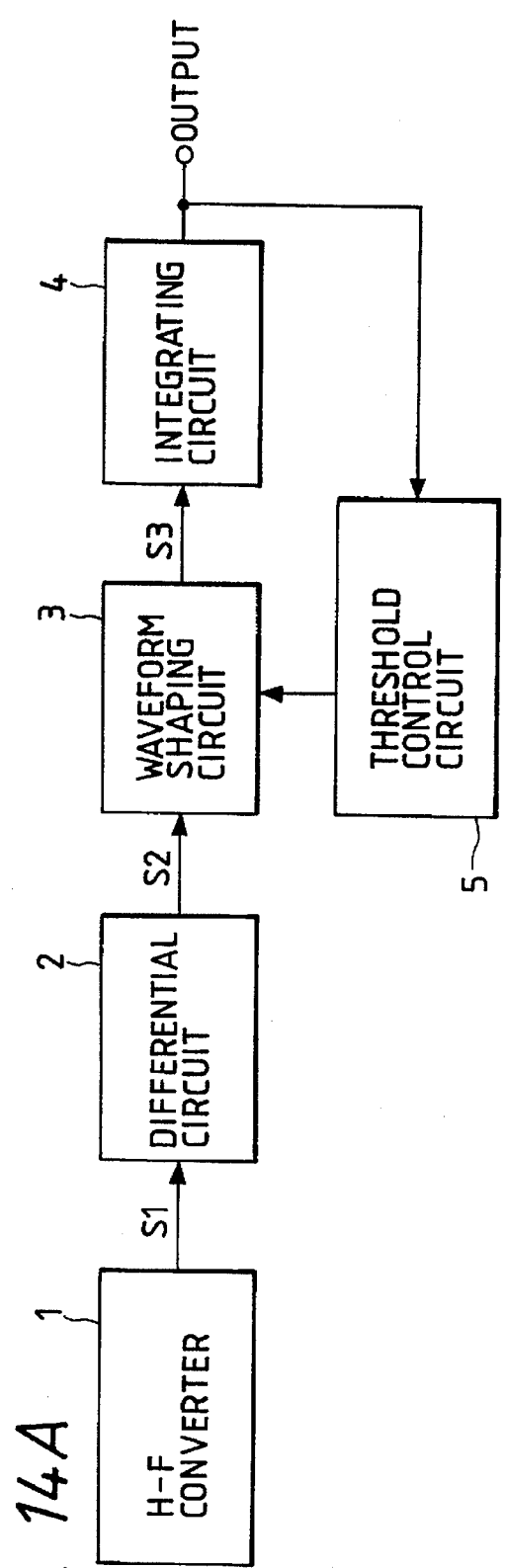
FIGS. 14A and 14B are diagrams illustrative of a conventional humidity meter.
Figure 14B:
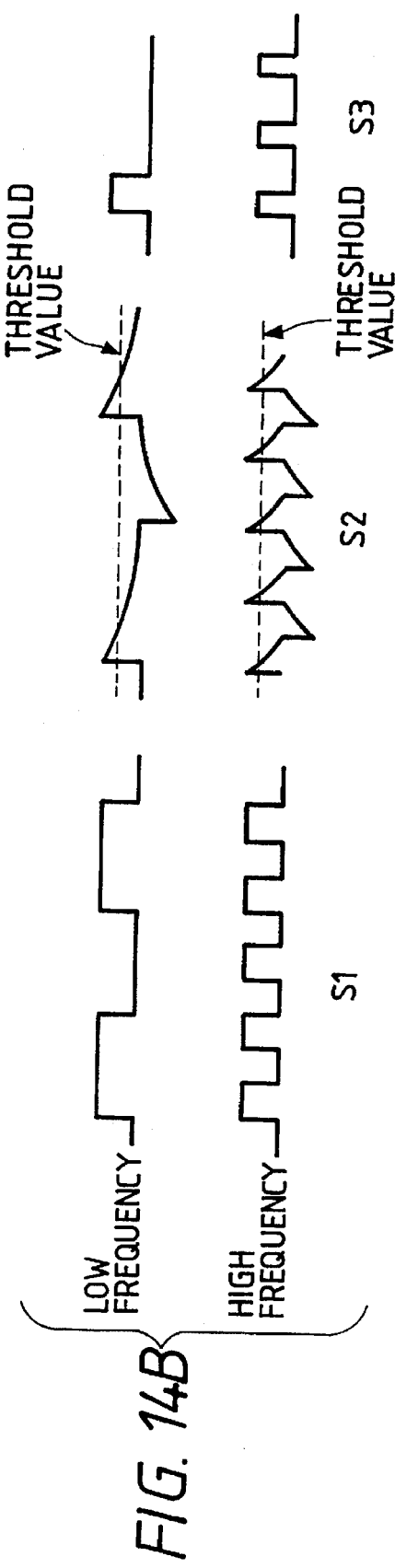

FIG. 13 presents exemplary measured data of the embodiments. FIG. 13A shows first exemplary measured data, and FIG. 13B shows second exemplary measured data. In these figures, the horizontal axis indicates relative humidity (RH %), and the vertical axis indicates output voltage (V).

The first exemplary measured data is an example in which measurements were made using the humidity meter according to the fourth embodiment (see FIG. 7). This humidity meter is characterized as connecting the series circuit consisting of the resistor $R_{17}$ and the capacitor $C_{13}$ to the output of the gate $G_{11}$.

Measurement was made while changing humidity at a temperature of 25.4° C. under the conditions that the resistance of the resistor $R_{17}$=6.8 KΩ; the resistance of the resistor $R_{14}$=2.0 KΩ; and the capacitance of the capacitor $C_{13}$=12000 pF. The output voltage under these conditions is equal to the voltage across the terminals $T_2$, $T_3$.

The data obtained as a result of such measurement exhibits an output characteristic with improved linearity as shown in diagram A. While the output voltage is somewhat decreased on the high humidity side, this will not affect the practical use of the humidity meter.

The second exemplary measured data is an example in which measurements were made using the humidity meter according to the fifth embodiment (see FIG. 10). This humidity meter is characterized as connecting both the series circuit consisting of the resistor $R_{17}$ and the capacitor $C_{13}$ and the series circuit consisting of the resistor $R_{19}$ and the capacitor $C_9$ in parallel to the output of the gate $G_{11}$.

Measurement was made while changing humidity at a temperature of 25.4° C. under the conditions that the resistance of the resistor $R_{17}$=8.2 KΩ; the resistance of the resistor $R_{19}$=7.2 KΩ; the capacitance of the capacitor $C_{13}$=1800 pF; the capacitance of the capacitor $C_{19}$=1200 pF; and the resistance of the resistor $R_{14}$=2.0 KΩ. The output voltage under these conditions is equal to the voltage across the terminals $T_2$, $T_3$.

The data obtained as a result of such measurement is as shown in diagram B. This data exhibits an output characteristic with further improved linearity compared with the data shown in diagram A, particularly with the decreased output voltage on the high humidity side in diagram A being improved.

Other embodiments

While the embodiments have been described in the foregoing pages, the invention may be embodied in the following way as well.

(1) A resistor may be connected in series with the thermistor Th in the humidity meter according to the third embodiment (see FIG. 6). Further, a plurality of thermistors Th may be used in this configuration.

(2) The oscillator circuits in the respective embodiments are not limited to those themselves described above, but may be any other similar oscillator circuits. However, it is essential that the oscillator circuit include a humidity sensor and an active element such as a C-MOS logic circuit in which the operating current increases with increasing operating frequency.

(3) In the fifth embodiment, three or more series circuits, each consisting of a resistor and a capacitor, may be connected to the gate $G_{11}$. However, it may be noted that the number of parts is increased in this configuration.

(4) The resistor $R_{14}$ in each of the fourth embodiment (see FIG. 7), the fifth embodiment (see FIG. 10), and the sixth embodiment (see FIG. 12) may be replaced with the thermistor Th shown in the third embodiment (see FIG. 6).

As described in the foregoing, the invention can provide the following advantages.

The humidity meter can be constructed of only the oscillator circuit including a humidity sensor (see the first embodiment). Therefore, the humidity meter of the invention can dispense with a differentiating circuit, a waveform shaping circuit, an integrating circuit, and a threshold circuit as has been required by the conventional humidity meter, thereby decreasing the number of parts accordingly. As a result, the humidity meter can be downsized, lightened, and made inexpensively.

The change in operating current due to a change in oscillating frequency can be amplified (increased) by adding a current change amplifying capacitor ($C_{13}$) to the oscillator circuit constituting the humidity meter (see the second and third embodiments). As a result, the humidity detecting accuracy of the humidity meter can be improved, and the output characteristic thereof can therefore be improved.

The change in operating current due to a change in the oscillating frequency of the oscillator circuit can be amplified (increased) by adding a current change amplifying capacitor ($C_{13}$) to the oscillator circuit constituting the humidity meter. In addition, an output limiting resistor ($R_{13}$) is inserted into the power supply circuit (see the second and third embodiments), so that the operating current is limited on the high humidity side to thereby improve the linearity of the output characteristic.

Since a thermistor is connected to the return of the power supply circuit (see the third embodiment), not only the operating current is converted into voltage but also temperature compensation on the output side of the humidity meter can be made. Therefore, a stable output voltage can be obtained with respect to a change in temperature.

Further, since the thermistor serves both as a current-voltage converter and a temperature compensator, the number of parts can be curtailed compared with humidity meters implementing such functions with separate parts. As a result, the humidity meter can be downsized and made inexpensively as well.

Not only the change in operating current due to a change in oscillating frequency can be amplified (increased), but also the increase in operating current on the high humidity side can be suppressed by connecting the series circuit (capacitive load) consisting of the current change amplifying capacitor and the resistor to the oscillator circuit constituting the humidity meter (see the fourth and sixth embodiments). As a result, the linearity of the output characteristic of the humidity meter can be improved.

Not only the change in operating current due to a change in oscillating frequency can be effectively amplified (increased), but also the increase in operating current on the high humidity side can be suppressed by connecting a plurality of series circuits (capacitive loads), each consisting of the current change amplifying capacitor and the resistor, to the oscillator circuit constituting the humidity meter (see the fifth embodiment). As a result, the linearity of the output characteristic of the humidity meter can be further improved.

Since the number of parts required is reduced to a significant extent, a humidity meter suitable for meeting the needs for downsizing, lightening, and cost reduction at the sacrifice of accuracy can be implemented.

What is claimed is:

1. A humidity meter comprising:

an oscillator circuit for providing an operating frequency including a humidity sensor changing electric impedance thereof responsive to humidity and an active circuit connected to said oscillator circuit and having the function of increasing an operating current with increasing operating frequency, wherein said active circuit includes two field effect transistors electrically connected in complementary mode, with each transistor having a first electrode connected to a common input, a second electrode connected to a common output and a third electrode connected to one terminal of a power supply;

wherein said oscillator circuit converts a change in humidity into a change in frequency, and where said active circuit converts the change in frequency into a change in operating current, and outputs the converted operating current as a measure of humidity in ambient air at the humidity sensor.

2. A humidity meter according to claim 1, further comprising a capacitor connected electrically to an output of said active circuit as a capacitive load in order to amplify the change in operating current resulting from the change in frequency.

3. A humidity meter according to claim 1, further comprising a series circuit consisting of a capacitor and a resistor connected electrically to an output of the active circuit as a capacitative load in order to amplify the change in operating current resulting from the change in frequency and to provide improved linearity of a sensor response over a broad range of humidity.

4. A humidity meter according to claim 1, further comprising a thermistor connected electrically to a return or negative terminal of a power supply circuit in order to not only convert the change in operating current into operating voltage but also make temperature compensation of humidity measurements made by said humidity meter.

5. A humidity meter according to claim 1, further comprising a plurality of series circuits, each consisting of a capacitor and a resistor, are connected electrically in parallel to an output of the active circuit as capacitive loads in order to amplify the change in operating current resulting from the change in frequency.

6. A humidity meter comprising:

an oscillator circuit for providing an operating frequency, including a humidity sensor changing electric impedance thereof responsive to humidity; and an active circuit connected to said humidity sensor and having a function of increasing an operating current with increasing operating frequency, wherein said active circuit includes two field effect transistors electrically connected in complementary mode, with each transistor having a first electrode connected to a common input, a second electrode connected to a common output and a third electrode connected to one terminal of a power supply;

wherein said oscillator circuit converts a change in humidity into a change in frequency, and said active circuit produces the operating current as a measure of humidity in ambient air at the humidity sensor in response to the change in frequency.

* * * * *